US00PP22739P3

(12) United States Plant Patent

Sarrazin et al.

(10) Patent No.: US PP22,739 P3

(45) Date of Patent: May 15, 2012

(54) *DICENTRA* PLANT NAMED 'HORDIVAL'

(50) Latin Name: *Dicentra spectabilis*
Varietal Denomination: HORDIVAL

(76) Inventors: Lyle Sarrazin, Prince George (CA); Phyllis Sarrazin, Prince George (CA)

( * ) Notice: Subject to any disclaimer, the term of this patent is extended or adjusted under 35 U.S.C. 154(b) by 0 days.

(21) Appl. No.: 12/802,098

(22) Filed: May 28, 2010

(65) Prior Publication Data

US 2011/0296573 P1 Dec. 1, 2011

(51) Int. Cl.
*A01H 5/00* (2006.01)

(52) U.S. Cl. ..... Plt./426

(58) Field of Classification Search ..... Plt./426
See application file for complete search history.

*Primary Examiner* — Kent L Bell

(74) *Attorney, Agent, or Firm* — Cassandra Bright

(57) ABSTRACT

A new and distinct *Dicentra spectabilis* cultivar named 'Hordival' is disclosed, characterized distinctive orange-red flowers, dark stems overall compact, shorter plants. The new variety is a *Dicentra spectabilis*, suitable for outdoor landscape and container use.

1 Drawing Sheet

Latin name of the genus and species: *Dicentra spectabilis*.
Variety denomination: 'HORDIVAL'.

BACKGROUND OF THE INVENTION

The new cultivar is the result of a chance discovery in a garden in Prince George, British Columbia, Canada. The inventors, Lyle and Phyllis Sarrazin, citizens of Canada, discovered the new variety as a naturally occurring chance seedling growing in a garden of the parent variety, the unpatented *Dicentra spectabilis*. The discovery was made in the Spring of 2005.

After selecting and isolating the new cultivar, asexual reproduction of the new cultivar 'HORDIVAL' was first performed by division during the Fall of 2005, in Prince George, British Columbia. 'HORDIVAL' has since produced several generations and has shown that the unique features of this cultivar are stable and reproduced true to type.

SUMMARY OF THE INVENTION

The cultivar 'HORDIVAL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HORDIVAL.' These characteristics in combination distinguish 'HORDIVAL' as a new and distinct *Dicentra* cultivar:

1. Dark Orange-Red flower.
2. Distinctive red stems.
3. Compact and overall shorter plant habit.

PARENTAL COMPARISON

Plants of the new cultivar 'HORDIVAL' are similar to the parent, in most horticultural characteristics. However, 'HORDIVAL' differs in having an over all more compact and shorter plant habit.

COMMERCIAL COMPARISON

Plants of the new cultivar 'HORDIVAL' are best compared to the parent variety.

BRIEF DESCRIPTION OF THE PHOTOGRAPH

The accompanying photograph in FIG. 1 illustrates in full color a typical plant of 'HORDIVAL' grown outdoors in the Netherlands This plant is approximately 1 year old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'HORDIVAL' plants grown outdoors in De Hoef, the Netherlands. Temperatures ranged from Approximately −10° C. to 30° C. day and night. No artificial light, photoperiodic treatments or chemical treatments were given to the plants. Measurements and numerical values represent averages of typical plant types.

Botanical classification: *Dicentra spectabilis* 'HORDIVAL'
Age of the plant described: Approximately 18 months
Container size of the plant described: 17 cm commercial container.

DETAILED BOTANICAL DESCRIPTION

PROPAGATION

Time to initiate roots: Typically propagated outdoors, from March to May. Root initiation takes approximately 10 days, with full rooting within 14 days.

Root description: Moderately dense, thin, slightly fleshy, slightly fibrous, coloured near RHS Grey-Brown 199D

PLANT

Growth habit: Broad inverted triangle.
Pot size of plant described: 17 cm.
Height: Average: 33.8 cm.
Plant spread: Average: 35.9 cm.
Growth rate: Moderately high
Branching characteristics: Basal branching with stem leaves and axillary and terminal racemes
Length of primary lateral branches: Average: 23.9 cm (excl. inflorescence).
Quantity of primary lateral branches: Average: 6.
Characteristics of primary lateral branches:
*Form.*—Rounded, slightly angled.
*Diameter.*—Average: 0.5 cm.
*Color.*—Near RHS Grey-Brown 200B, slightly tinged RHS Greyed-Green 197A.
*Texture.*—Smooth, dull due to a waxy layer.
*Strength.*—Moderately weak.
Internode length: Average: 5.3 cm.

FOLIAGE

Leaf:
*Arrangement.*—Alternate.
*Leaves.*—Shape: Compound, biternate (broad ovate in outline). Quantity: Approximately 9 per branch. Average Length: 14.6 cm. Average Width: 9.4 cm.
*Individual leaf blades* (*leaflets*).—Average Length: 5.1 cm. Average Width: 3.2 cm. Shape of blade: Trifoliate (obovate to orbicular in outline). Apex: Apiculate. Base: Short attenuate. Margin: Coarsely serrate. Texture of top surface: Smooth, very slightly glossy. Pubescence: No.
*Aspect.*—Leaf blades slightly concave, leaflets slightly drooping in an average angle of −20° (0°=horizontal).
*Color.*—Young foliage upper side: Near RHS Yellow-Green 144B. Young foliage under side: Near RHS Yellow-Green 145A. Mature foliage upper side: Near RHS Green 137B. Mature foliage under side: Near RHS Yellow-Green 147B, slightly tinged Greyed-Purple 183D.
*Venation.*—Type: Pinnate. Venation color upper side: Near RHS Greyed-Red 182A. Venation color under side: Near RHS Greyed-Purple 183B.
*Petiole.*—Length: Average 9.4 cm. Diameter: Average 0.3 cm. Color: Near RHS Greyed-Orange 177A. Texture: Smooth, dull due to a waxy layer.
*Stipule description* (*if present*).—No stipules present.

INFLORESCENCE

Natural flowering season: Spring
Days to flowering from a rooted plantlet: Sparse initial flowering several weeks after rooting. Full flowering after plants are 1 year old, starting in March.
Inflorescence and flower type and habit: Individual flowers in axillary and terminal racemes
Inflorescence dimensions:
*Diameter.*—Average 5.9 cm.
*Length.*—Average 11.2 cm.
Rate of flower opening: 5 to 8 days from bud to fully opened flower.
Flower longevity on plant: Average: one week
Persistent or self-cleaning: Self-cleaning
Bud:
*Shape.*—Obovate.
*Length.*—1.0 cm.
*Diameter.*—0.3 cm.
*Color.*—Near RHS Yellow-Green 152C.
Flower size:
*Diameter.*—At widest: 2.1 cm; at narrowest: 0.8 cm.
*Depth.*—2.7 cm.
*Aspect.*—Drooping, in an average angle of −20° (0°=horizontal).
*Flowers per inflorescence.*—Average 6.
Petals:
*Quantity.*—4.
*Arrangement.*—2 oppositely placed pairs of similar petals.
*Length.*—Two narrowest petals average: 2.2 cm. Two widest petals average: 1.8 cm.
*Width.*—Narrowest petal average: 0.35 cm. Widest petal average: 1.0 cm.
*Shape.*—Narrowest petals lanceolate, fused at the tips. Widest petals orbicular, but folded.
*Apex.*—All petals have an acute apex.
*Base.*—All petals have a cuneate base.
*Margin.*—Entire.
*Texture, upper and lower surfaces.*—Dull, smooth, non-pubescent.
*Color.*—When opening, upper surface: Narrowest petal; Near RHS White N155D, base near RHS Greyed-Purple 187A. Widest petal; near RHS Red 54C, tip darker; 54B, outer tip Yellow-Green 148A. When opening, lower surface: Narrowest petal; near RHS White N155D, Base near RHS Greyed-Purple 187A. Widest petal; RHS Red 55C, tip Yellow-Green 148B. Fully opened, upper surface: Narrowest petal; RHS White N155D, base RHS Greyed-Purple 187A. Widest petal; RHS Red 54C, tip darker; 54B, outer tip Yellow-Green 148A. Fully opened, lower surface: Narrowest petal; RHS White N155D, base RHS Greyed-Purple 187A. Widest petal; RHS Red 55C, tip Yellow-Green 148B.
Bracts (if present): No bracts present
Sepals: No separate petals and sepals present, only petals (see above)
Peduncles:
*Length.*—9.4 cm.
*Diameter.*—0.2 cm.
*Angle.*—About 45° to the lateral branch.
*Strength.*—Moderate.
*Texture.*—Smooth, dull due to a waxy layer.
*Color.*—Near RHS Brown 200A, tinged Greyed-Purple N186C.
Pedicels:
*Length.*—1.1 cm.
*Diameter.*—0.05 cm.
*Angle.*—About 45° to the peduncle, =about 90° to the lateral branch.
*Strength.*—Moderate.
*Texture.*—Smooth, dull due to a waxy layer.
*Color.*—Near RHS Brown 200B.
Fragrance: No fragrance.

REPRODUCTIVE ORGANS

Stamens:

*Number.*—6, fused in two groups of three, one on each side of the ovary, covered by the two narrowest petals.

Anthers:

*Shape.*—Anthers basifixed, narrow oblong, filament curved, following the shape of the narrowest petals.

*Length.*—Anthers approximately 0.1 cm. Filaments approximately 2.0 cm.

*Color.*—Anther: Near RHS Yellow 12A. Filaments: Near RHS Red 56D.

*Pollen.*—Color: Near RHS Yellow 11B. Quantity: Moderate.

Pistil:

*Number.*—1.

*Length.*—1.9 cm.

*Style.*—Length: 1.0 cm. Color: Near RHS Yellow-Green 145B.

*Stigma.*—Shape: Umbraculate. Color: Near RHS Yellow-Green 153D. Ovary Color: Near RHS Yellow-Green 145A.

OTHER CHARACTERISTICS

Seeds and fruits: Not observed to date.

Disease/pest resistance: Neither resistance nor susceptibility to normal diseases and pests of *Dicentra* has been observed.

Temperature tolerance: The new variety tolerates low temperatures to at least USDA Zone 4, and has been observed to tolerate high temperatures to 35° C.

What is claimed is:

1. A new and distinct cultivar of *Dicentra* a plant named 'Hordival' as herein illustrated and described.

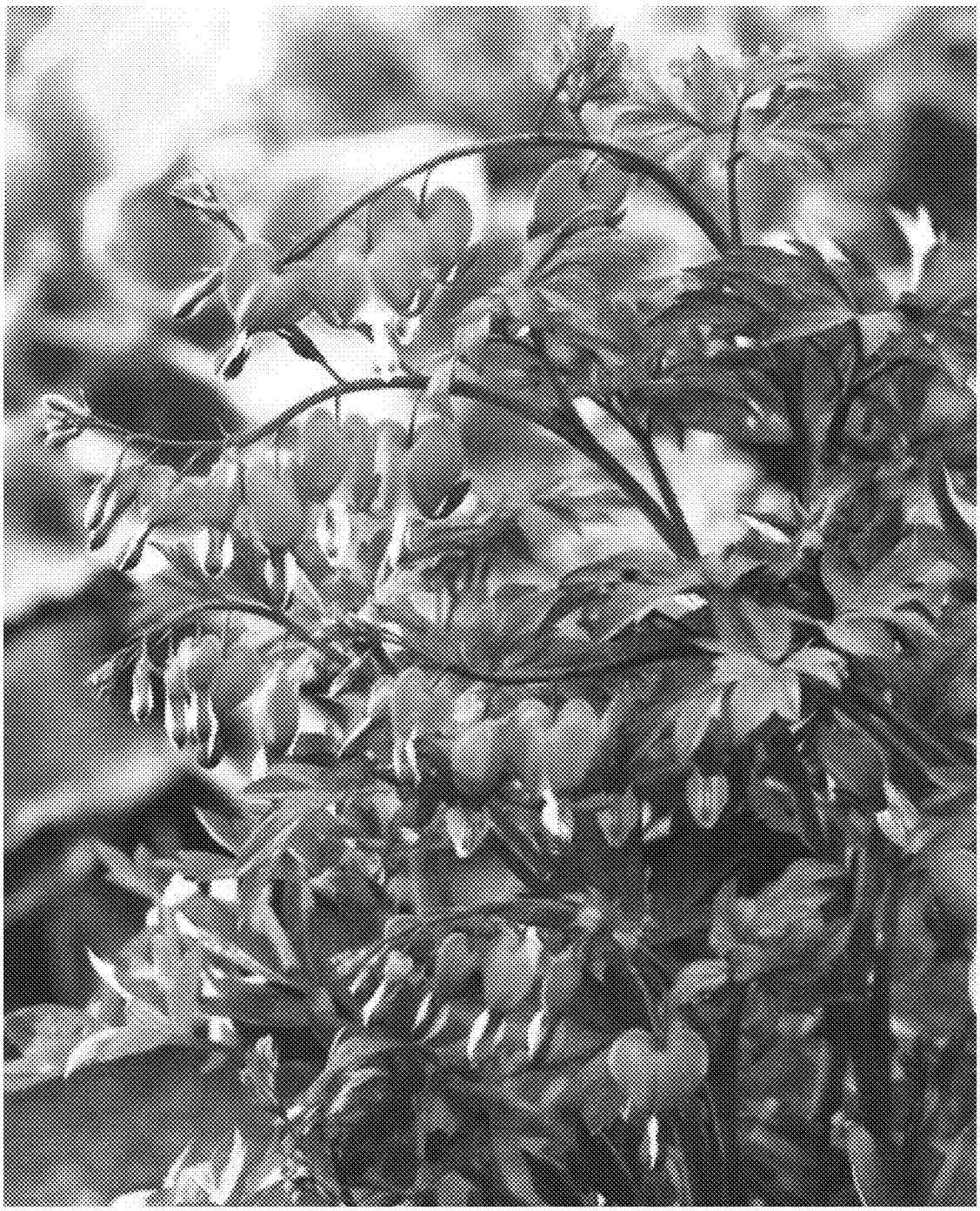

* * * * *